Patent Number: 5,100,987
Date of Patent: Mar. 31, 1992

[54] MONOETHYLENICALLY UNSATURATED COMPOUNDS WHOSE POLYMERS ARE USEFUL AS PHOTOINITIATORS

[75] Inventors: Kevin B. Hatton, Cambridge; Edward Irving, Burwell; Josephine M. A. Walshe, Girton; Anne Mallaband, Bishops Stortford, all of England

[73] Assignee: Ciba-Geigy Corporation, Ardsley, N.Y.

[21] Appl. No.: 603,092

[22] Filed: Oct. 25, 1990

Related U.S. Application Data

[60] Division of Ser. No. 465,513, Jan. 16, 1990, Pat. No. 4,977,293, which is a continuation of Ser. No. 224,624, Jul. 27, 1988, abandoned.

[30] Foreign Application Priority Data

Aug. 5, 1987 [GB] United Kingdom ............... 8718496
May 25, 1988 [GB] United Kingdom ............... 8812386

[51] Int. Cl.$^5$ ............................................. C08F 18/24
[52] U.S. Cl. ........................................ 526/313; 526/314
[58] Field of Search ................................ 526/314, 313

[56] References Cited

U.S. PATENT DOCUMENTS

| | | | |
|---|---|---|---|
| 4,082,821 | 4/1978 | Schmidt et al. | 260/946 |
| 4,088,554 | 5/1978 | Felder et al. | 204/159.15 |
| 4,272,457 | 6/1981 | Poisson et al. | 260/953 |
| 4,308,400 | 12/1981 | Felder et al. | 568/336 |
| 4,310,687 | 1/1982 | Barabas et al. | 560/221 |
| 4,559,371 | 12/1985 | Hüsler et al. | 204/159.18 |
| 4,582,862 | 4/1986 | Berner et al. | 522/14 |
| 4,592,816 | 6/1986 | Emmons et al. | 204/180.6 |
| 4,977,293 | 12/1990 | Hatton et al. | 558/153 |

FOREIGN PATENT DOCUMENTS 217205 9/1982 European Pat. Off.

OTHER PUBLICATIONS

Derwent Abstract, 86-278795.

Primary Examiner—Joseph L. Schofer
Assistant Examiner—Jeffrey T. Smith
Attorney, Agent, or Firm—JoAnn Villamizar

[57] ABSTRACT

Monethylenically unsaturated compounds whose polymers are useful as polymeric photoinitiators are of formula $Ar^1COC(R^1)(R^2)R^3$ where $R^1$ is $C_1$-$C_{10}$ alkyl or alkoxy, $R^2$ is $C_1$-$C_{10}$ alkyl, $-X-O-R^4-OCOC(R^5)=CH_2$ (II) $-X-NH-R^6-OCOC(R^5)=CH_2$ (III), or $-CH_2[OCH_2CH(OH)CH_2]_aOCOC(R^5)=CH_2$ (IIIA) or $R^1$ and $R^2$, together with the attached carbon, denote $C_4$-$C_8$ cycloalkyl, $R^3$ is a $C_6$-$C_{20}$ aromatic group, OH, tert.amino, $-OCOC(R^5)=CH_2$ (VI) or $-OCH_2CH(OH)CH_2OCOC(R^5)=CH_2$ (VIA), $R^4$ is $C_1$-$C_4$ alkylene, which may be substituted by $-OH$ or by $C_2$-$C_{20}$ acyloxy, $R^5$ is H or $C_1$-$C_4$ alkyl, $R^6$ is $C_1$ to $C_4$ alkylene, X is a group of formula $R^7CO-$ or

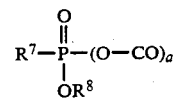

where $R^7$ is $C_1$-$C_4$ alkylene, $R^8$ is $C_1$ to $C_4$ alkyl, and is 0 or 1, $Ar^1$ is a $C_6$-$C_{20}$ aromatic group, with the provisos that (i) $R^2$, $R^3$ or $Ar^1$ contains a group (VI), (ii) where $R^1$ and $R^2$ together with the attached carbon atom denote cycloalkyl, $R^3$ is $-OH$, tert.amino or a group VI or VIA (iii) when $R^2$ is a group II, a is 0, (iv) when $R^2$ is a group III a is 1, (v) when $R^2$ denotes a group IIIA, $R^3$ denotes said monovalent aromatic group (vi) when $R^3$ denotes a group VI, $R^1$ and $R^2$ together with the attached carbon denote $C_4$-$C_8$ cycloalkyl, (vii) when $Ar^1$ contains a group VI $R^1$ is $-CH_3$ and $R^3$ is $-OH$, $R^2$ is $C_2$-$C_{10}$ alkyl, and (viii) when $Ar^1$ contains a group VI, $R^1$ and $R^2$ are each alkyl and $R^3$ is $-OH$, the group VI is linked to an aromatic C atom in $Ar^1$ through a group $-YR^{10}OR^9-$ or $-YR^{10}OCONH-R^6-$, Y being attached to an aromatic C atom, where Y is O or S, $R^9$ is 2-hydroxypropylene or 2-($C_2$-$C_{20}$ acyloxy)propylene and $R^{10}$ is $C_1$-$C_4$ alkylene.

9 Claims, No Drawings

MONOETHYLENICALLY UNSATURATED COMPOUNDS WHOSE POLYMERS ARE USEFUL AS PHOTOINITIATORS

This is a divisional of application Ser. No. 465,513, filed on Jan. 16, 1990, now U.S. Pat. No. 4,977,293, which is a continuation of Ser. No. 224,624, filed on July 27, 1988, now abandoned.

This invention relates to monoethylenically unsaturated compounds and their polymers. The polymers are useful in electrodepositable photoresist compositions.

U.S. Pat. No. 4,592,816 proposes the electrodeposition of a photoresist film from an aqueous solution or emulsion containing a mixture of a positively or negatively charged polymer, a multifunctional acrylate or methacrylate as photocrosslinking monomer and a photoinitiator. While use of an electrodeposition bath containing such a mixture can initially give satisfactory images, after a small number of electrodepositions have been carried out the electrodeposited film does not form a satisfactory image, even on exposure to radiation for considerably longer than the initially deposited film.

It has now been found that images suitable for use in printed circuits and printing plates can be formed with good reproducibility by electrodeposition from a composition containing a multifunctional acrylate or methacrylate and a polymer having in the same molecule a photopolymerization-initiating residue and a salt-forming group. It has further been found that polymers suitable for use in such compositions can be obtained from certain acrylic monomers containing photopolymerization-initiating residues.

In W. German Offenlegungsschrift 3 534 645 there are described compounds of formula

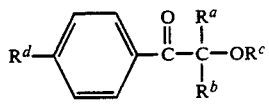

where
- $R^a$ and $R^b$ each denote H, $C_1$–$C_6$ alkyl or phenyl,
- $R^c$ denotes H, $C_1$–$C_6$ alkyl, $C_1$–$C_6$ alkanoyl or a group Z,
- $R^d$ denotes H, halogen, $C_1$–$C_{12}$ alkyl, $C_1$–$C_{12}$ alkoxy, $C_1$–$C_{12}$ alkylthio or a group $-[X^a-(CH_2-CH_2-O)_n-Z^a]_m$,
- $X^a$ denotes O, S or N,
- n denotes 0 to 4,
- m denotes 1 when $X^a$ is O or S and 1 or 2 when $X^a$ is N,
- Z denotes $-CO-CR=CR'R''$ where R, R' and R'' each denote H or $CH_3$, and
- at least one of $R^c$ and $R^d$ contains the group Z.

The compounds described in the cited publication are said to be useful for the photopolymerization of ethylenically unsaturated compounds. They tend, however, to have relatively low activity and are difficult to thermally copolymerize to give linear photosensitive polymers. Compounds of this invention can effect rapid photocure and can be readily thermally copolymerized with other monomers to give polymers of good photosensitivity useful as photoinitiators in electrodepositable photoresists.

Accordingly, the present invention provides a monoethylenically unsaturated compound of formula

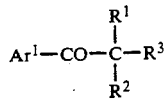

where
- $R^1$ denotes an alkyl or alkoxy group of 1 to 10 carbon atoms,
- $R^2$ denotes an alkyl group of 1 to 10 carbon atoms or a group of formula II, III or IIIA $$-X-O-R^4-OCOC(R^5)=CH_2 \quad\quad II$$

$$-X-NH-R^6-OCOC(R^5)=CH_2 \quad\quad III$$

$$-CH_2[OCH_2CH(OH)CH_2]_aOCOC(R^5)=CH_2 \quad\quad IIIA$$

or $R^1$ and $R^2$, together with the carbon atom to which they are attached, denote a cycloalkyl group of 4 to 8 carbon atoms,
- $R^3$ denotes a monovalent aromatic group of 6 to 20 carbon atoms linked through an aromatic carbon atom to the indicated carbon atom, a hydroxyl group, a tertiary amine group linked through the amino nitrogen atom to the indicated carbon atom, or a group of formula VI or VIA $$-OCOC(R^5)=CH_2 \quad\quad VI$$

$$-OCH_2CH(OH)CH_2OCOC(R^5)=CH_2 \quad\quad VIA$$

- $R^4$ denotes an alkylene group of 1 to 4 carbon atoms, which is unsubstituted or substituted by a hydroxyl group or by an acyloxy group of 2 to 20 carbon atoms,
- $R^5$ denotes a hydrogen atom or an alkyl group of 1 to 4 carbon atoms,
- $R^6$ denotes an alkylene group of 1 to 4 carbon atoms,
- X denotes a group of formula IV or V $$-R^7CO- \quad\quad VI$$

- $R^7$ denotes an alkylene group of 1 to 4 carbon atoms,
- $R^8$ denotes an alkyl group of 1 to 4 carbon atoms,
- a denotes zero or 1, and
- $Ar^1$ denotes a monovalent aromatic group of 6 to 20 carbon atoms linked through an aromatic carbon atom to the indicated carbonyl group, with the provisos that
(i) $R^2$, $R^3$ or $Ar^1$ contains a group of formula $$-OCOC(R^5)=CH_2 \quad\quad VI$$

(ii) when $R^1$ and $R^2$, together with the carbon atom to which they are attached, denote a cycloalkyl group, $R^3$ denotes a hydroxyl group, said tertiary amine group or a group of formula VI or VIA,
(iii) when $R^2$ denotes a group of formula II, a denotes zero,
(iv) when $R^2$ denotes a group of formula III, a denotes 1, (v) when $R^2$ denotes a group of formula IIIA, $R^3$ denotes said monovalent aromatic group of 6 to 20 carbon atoms, (vi) when $R^3$ denotes a group of formula VI, $R^1$ and $R^2$, together with the carbon atom to which they are attached, denote a cycloalkyl group of 4 to 8 carbon atoms, (vii) when $Ar^1$ contains a group of formula VI, $R^1$ denotes a methyl group and $R^3$ denotes a hydroxyl group, then $R^2$ denotes an alkyl group of 2 to 10 carbon atoms, and (viii) when $Ar^1$ contains a group of formula VI, $R^1$ and $R^2$ each denote an alkyl group and $R^3$ denotes a hydroxyl group, then the group of formula VI is linked to an aromatic carbon atom in $Ar^1$ through a group of formula $-Y-R^{10}-O-R^9-$ or $-Y-R^{10}-OCONHR^6-$, the indicated $-Y-$ group being linked directly to an aromatic carbon atom in $Ar^1$, where Y denotes an oxygen or sulphur atom, $R^9$ denotes a 2-hydroxypropylene group or a 2-acyloxypropylene group where the acyloxy group contains 2 to 20 carbon atoms and $R^{10}$ denotes an alkylene group of 1 to 4 carbon atoms.

In formula I, $R^1$ may be, for example, a methyl group, a methoxy group, a pentyl group or an octyloxy group. Preferably, $R^1$ denotes an alkyl group of 1 to 4 carbon atoms, which may be a methyl, ethyl, n-propyl, isopropyl, n-butyl, sec.butyl or tert.-butyl group, or an alkoxy group of 1 to 4 carbon atoms which may be a methoxy, ethoxy, n-propoxy, isopropoxy, n-butoxy, sec.butoxy or tert.butoxy group. Particularly preferred groups $R^1$ are methyl, methoxy and ethoxy groups.

When $R^2$ denotes an alkyl group, it may be, for example, a methyl group, a hexyl group or octyl group, preferably an alkyl group of 1 to 4 carbon atoms which may be a methyl, ethyl, n-propyl, isopropyl, n-butyl, sec.butyl or tert.butyl group. Where $R^2$ denotes a group of formula II or III, $R^4$ in formula II may be a methylene, ethylene, propylene or butylene group or a propylene or butylene group substituted by a hydroxyl group or by an acetoxy, propionyloxy, hexanoyloxy, octanoyloxy, dodecanoyloxy, hexahydrobenzoyloxy or benzoyloxy group, $R^6$ in formula III may be a methylene, ethylene, propylene or butylene group and X may be a group of formula IV or V where $R^7$ may be a methylene, ethylene, propylene or butylene group and where $R^8$ may be a methyl, ethyl, propyl or butyl group.

Preferably, $R^2$ denotes a group of formula IIIA, an alkyl group of 1 to 4 carbon atoms or a group of formula II or III where $R^4$ denotes a group of formula $$-CH_2CH(OH)CH_2- \qquad \text{VII}$$

$R^6$ denotes an ethylene or propylene group and X denotes a group of formula IV or V where $R^7$ denotes an ethylene or propylene group and $R^8$ denotes a methyl or ethyl group. In particularly preferred embodiments, $R^2$ denotes a methyl or ethyl group, a group of formula II or III where $R^6$ and $R^7$ each denote an ethylene group and $R^8$ denotes an ethyl group, or a group of formula IIIA.

In embodiments where $R^1$ and $R^2$, together with the carbon atom to which they are attached, denote a cycloalkyl group, that group may be a cyclobutyl, cyclopentyl, cyclohexyl, cycloheptyl, or cyclooctyl group, that is $R^1$ and $R^2$ together may denote a propylene, butylene, pentylene, hexylene or heptylene group. Preferably, $R^1$ and $R^2$ together with the carbon atom to which they are attached denote a cyclopentyl or, particularly, a cyclohexyl group.

Where $R^3$ denotes a monovalent $C_6$-$C_{20}$ aromatic group, it may be, for example, a phenyl group, which may be unsubstituted or substituted, for instance, by a halogen atom or an alkyl or alkoxy group of 1 to 4 carbon atoms. Where $R^3$ denotes a tertiary amine group, it usually contains 2 to 12 carbon atoms. It may be a dialkylamino group, where each alkyl group contains from 1 to 6 carbon atoms and may be substituted by a hydroxyl group, for example a dimethylamino, diethylamino, or di(hydroxyethyl)amino group; or it may be a nitrogen heterocyclic group linked through a ring tertiary nitrogen atom to the indicated carbon atom in formula I, for example a pyrrolidine, piperidine, morpholine or a 4-alkylpiperazine group. Preferably, $R^3$ denotes a phenyl group, a monovalent nitrogen heterocyclic group of 4 to 5 carbon atoms linked through a ring tertiary nitrogen atom to the indicated carbon atom in formula I, or a group of formula VI or VIA. Particularly preferred groups $R^3$ are unsubstituted phenyl, N-morpholino and a group of formula VI.

$Ar^1$ may denote, for example, a phenyl group, which may be unsubstituted or substituted, for example, by an alkyl, alkoxy, or alkylthio group of 1 to 4 carbon atoms, such as a methyl, ethyl, propyl, butyl, methoxy, ethoxy or methylthio group, by a halogen atom or by a group terminated by a group of formula VI. Preferably, $Ar^1$ denotes a phenyl group which is unsubstituted or is substituted by an alkyl, alkoxy or alkylthio group of 1 to 4 carbon atoms, or by a group of formula VIII or IX:

$$-Y-R^{10}-(OR^{11})_m-OCOC(R^5)=CH_2 \qquad \text{VIII}$$

$$-Y-R^{10}OCONHR^6OCOC(R^5)=CH_2 \qquad \text{IX}$$

where $R^5$ and $R^6$ are as hereinbefore defined, $R^{10}$ denotes an alkylene group of 1 to 4 carbon atoms, $R^{11}$ denotes an alkylene group of 1 to 4 carbon atoms which is unsubstituted or substituted by a hydroxyl group or by an acyloxy group of 2 to 20 carbon atoms, Y denotes an oxygen or sulphur atom and m denotes 0 or 1.

In formulae VIII and IX, $R^6$, $R^{10}$ and $R^{11}$ may each be a methylene, ethylene, propylene or butylene group; $R^{11}$ may also be a propylene or butylene group substituted by a hydroxyl group.

In particularly preferred embodiments, $Ar^1$ denotes a phenyl group which is unsubstituted or substituted by a group of formula VIII or IX where $R^6$ and $R^{10}$ each denote an ethylene group, $R^{11}$ denotes a group of formula VII:

$$-CH_2CH(OH)CH_2- \qquad \text{VII}$$

and m denotes 1.

$R^5$ may denote a hydrogen atom or a methyl, ethyl, propyl or butyl group. In particularly preferred compounds $R^5$ denotes a hydrogen atom or a methyl group, that is the group of formula VI denotes an acryloyloxy or methacryloyloxy group.

Specific especially preferred compounds of formula I where $R^5$ denotes a hydrogen atom or a methyl group include:

(a) those in which $R^1$ denotes a methoxy group,
$R^2$ denotes a group of formula X or XI $$-CH_2CH_2CONHCH_2CH_2OCOC(R^5)=CH_2 \quad \text{X}$$

$$-CH_2CH_2COOCH_2CH(OH)CH_2OCOC(R^5)=CH_2 \quad \text{XI}$$

and
$R^3$ and $Ar^1$ each denote an unsubstituted phenyl group;

(b) those in which
$R^1$ denotes a methoxy or ethoxy group,
$R^2$ denotes a group of formula $$-CH_2CH_2-\underset{\underset{OCH_2CH_3}{|}}{\overset{\overset{O}{\|}}{P}}-OCH_2CH(OH)CH_2OCOC(R^5)=CH_2 \quad \text{XII}$$

and $R^3$ and $Ar^1$ each denote an unsubstituted phenyl group;

(c) those in which
$R^1$ and $R^2$ each denote a methyl group,
$R^3$ denotes a N-morpholino group and
$Ar^1$ denotes phenyl substituted by a group of formula XIII or XIV:

$$-SCH_2CH_2OCONHCH_2CH_2OCOC(R^5)=CH_2 \quad \text{XIII}$$

$$-SCH_2CH_2OCH_2CH(OH)CH_2OCOC(R^5)=CH_2 \quad \text{XIV}$$

(d) those in which
$R^1$ and $R^2$ together with the carbon atom to which they are attached denote a cyclohexyl group,
$R^3$ denotes a group of formula VI:

$$-OCOC(R^5)=CH_2 \quad \text{VI}$$

and
$Ar^1$ denotes an unsubstituted phenyl group; and (e) a compound in which
$R^1$ denotes a methoxy group,
$R^2$ denotes a group of formula $$-CH_2OCOC(R^5)=CH_2 \quad \text{XIVA}$$

and
$R^3$ and $Ar^1$ each denote an unsubstituted phenyl group.

The present invention also provides processes for the preparation of compounds of formula I.

A process for the preparation of a compound of formula I, in which $R^2$ denotes a group of formula II or III, where $R^4$ denotes a group of formula $-CH_2CH(OH)CH_2-$ and X denotes a group of formula IV, comprises reacting a compound of formula $$\underset{\underset{R^7-COOH}{|}}{Ar^1-CO-\overset{\overset{R^1}{|}}{C}-R^3} \quad \text{XV}$$

with either
(i) a glycidyl ester of formula $$\underset{\underset{O}{\diagdown\diagup}}{CH_2-CHCH_2OCOC(R^5)=CH_2} \quad \text{XVI}$$

or
(ii) an isocyanatoalkyl ester of formula $$OCN-R^6-OCOC(R^5)=CH_2 \quad \text{XVII}$$

where
$R^1$ denotes an alkyl or alkoxy group of 1 to 10 carbon atoms,
$R^3$ denotes a $C_6$-$C_{20}$ aromatic group or a hydroxyl group, $R^5$, $R^6$ and $R^7$ are as hereinbefore defined and
$Ar^1$ is as hereinbefore defined and is free from ethylenic unsaturation.

The reaction between the carboxylic acid of formula XV and the glycidyl ester of formula XVI may be carried out under conventional conditions for carboxyl-epoxide reactions where one of the reactants contains polymerisable acrylic unsaturation. For instance, the carboxylic acid and the glycidyl ester may be heated together, usually in an inert organic solvent, at temperatures from 40° to 140° C. in the presence, as catalyst, of a tertiary amine, an onium salt or a chromium carboxylate. The reaction is usually carried out in the presence of a polymerisation inhibitor, for example a sterically hindered phenol such as 2,6-di-tert.butyl-p-cresol, to prevent polymerisation of the acrylic group.

Reaction between the carboxylic acid of formula XV and the isocyanatoalkyl ester of formula XVII may be effected using conventional methods for carboxyl-isocyanate reactions. For example, the carboxylic acid and the isocyanatoalkyl ester may be stirred together in an inert organic solvent at ambient temperatures in the presence of a tertiary amine as catalyst.

A process for the preparation of a compound of formula I in which $R^2$ denotes a group of formula II or III, where $R^4$ denotes a group of formula $-CH_2CH(OH)CH_2-$ and X denotes a group of formula V, comprises reacting a compound of formula $$\underset{\underset{OR^8}{|}}{\underset{\underset{O=P-OH}{|}}{\underset{\underset{R^7}{|}}{Ar^1-CO-\overset{\overset{R^1}{|}}{\underset{|}{C}}-R^3}}} \quad \text{XVIII}$$

with either a glycidyl ester of formula XVI as hereinbefore defined or an isocyanatoalkyl ester of formula XVII as hereinbefore defined
where
$R^1$ denotes an alkyl or alkoxy group of 1 to 10 carbon atoms,
$R^3$, $R^7$ and $R^8$ are as hereinbefore defined and
$Ar^1$ is as hereinbefore defined and is free from ethylenic unsaturation.

The reaction between the compound of formula XVIII and the glycidyl ester may be carried out under conventional conditions for hydroxyl-epoxide reactions where one of the reactants contains a polymerisable acrylic group. For instance, the reaction may be carried out using the process hereinbefore described for the reaction of the carboxylic acid of formula XV with the glycidyl ester.

Reaction between the compound of formula XVIII and the isocyanatoalkyl ester may be effected using conventional methods for hydroxyl-isocyanate reactions, for example by heating the reactants together, at a temperature from 30° to 130° C., in an inert solvent in the presence of a tin carboxylate salt as catalyst.

Another process for the preparation of a compound of formula I comprises reacting a compound of formula

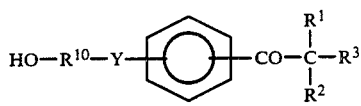   XIX with either a glycidyl ester of formula XVI or an isocyanatoalkyl ester of formula XVII, where $R^1$ denotes an alkyl or alkoxy group of 1 to 10 carbon atoms, $R^2$ denotes an alkyl group of 1 to 10 carbon atoms, or $R^1$ and $R^2$ together with the carbon atom to which they are attached denote a $C_4$ to $C_8$ cycloalkyl group, $R^3$ is as hereinbefore defined, $R^{10}$ denotes an alkylene group of 1 to 4 carbon atoms and Y denotes an oxygen or sulphur atom.

The reactions between the compound of formula XIX and the glycidyl ester or isocyanatoalkyl ester may be carried out under conventional conditions for hydroxyl-epoxide or hydroxyl-isocyanate reactions respectively, for example the methods described above for reaction of the glycidyl ester or isocyanatoalkyl ester with a compound of formula XVIII.

Carboxylic acids of formula XV can be prepared by a Michael addition reaction of a compound of formula

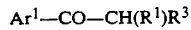   XX such as a benzoin alkyl ether, with an ester of an unsaturated carboxylic of formula

   XXI where $Ar^1$, $R^1$ and $R^3$ are as defined in formula XV, and $R^{12}$ denotes an alkenyl group of 2 to 4 carbon atoms, in the presence of an alkaline catalyst, followed by hydrolysis of the resulting ester.

Carboxylic acids of formula XV can also be prepared by reaction of a compound of formula XX with an aldehyde of formula

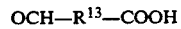   XXII where $R^{13}$ denotes an alkylene group of 1 to 3 carbon atoms, in the presence of an alkaline catalyst.

Compounds of formula XVIII can be prepared by a Michael addition reaction, in the presence of an alkaline catalyst, of a compound of formula XX, such as a benzoin alkyl ether, with an unsaturated phosphonic acid dialkyl ester of formula

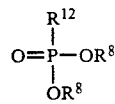   XXIII where $R^8$ and $R^{12}$ are as hereinbefore defined, as described in U.S. Pat. No. 4,082,821, followed by hydrolysis of one of the groups —$OR^8$ in the resulting ester. This hydrolysis may conveniently be effected by heating together with sodium hydroxide or potassium hydroxide in solution in ethanol or methanol.

Compounds of formula XIX where $R^1$ and $R^2$ each denote $C_1$ to $C_{10}$ alkyl, $R^3$ denotes an aromatic group and Y denotes —S— can be prepared by reacting an acid chloride of formula

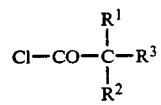   XXIV with a halobenzene, usually chlorobenzene or bromobenzene, under conventional Friedel-Crafts reaction conditions to give an intermediate of formula

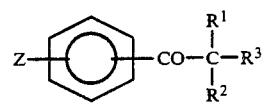   XXV where Z denotes —Cl or —Br, and heating the intermediate with 2-mercaptoethanol in the presence of a strong base such as an alkali metal hydroxide or carbonate, usually in a polar solvent such as dimethylformamide or dimethyl sulphoxide, to replace —Z by —$SCH_2CH_2OH$.

Analogous compounds of formula XIX where Y denotes —O— can be prepared by reacting the acid chloride of formula XXIV with anisole to give an intermediate analogous to that of formula XXV, but with Z— being replaced by $CH_3O$—, reacting the intermediate with hydrobromic acid to convert the methoxy group to hydroxyl and then reacting the hydroxyl group with chloroethanol or ethylene oxide.

Compounds of formula XIX where $R^3$ denotes a hydroxyl group can be prepared by the process described in published PCT Application WO 86/05778. Compounds of formula XIX where $R^3$ denotes a tertiary amino group and Y denotes —S—, and the preparation of such compounds, are described in U.S. Pat. No. 4,582,862. Analogous compounds where Y denotes —O—, and their preparation, are described in U.S. Pat. No. 4,559,371.

Compounds of formula I where $R^1$ and $R^2$, together with the carbon atom to which they are attached, denote a cycloalkyl group and $R^3$ denotes a group of formula VI can be prepared by reacting, usually under conventional conditions for hydroxyl-acid reactions, a compound of formula

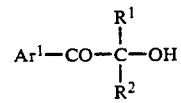   XXVI with an acid chloride of formula

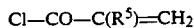 Cl—CO—C(R$^5$)=CH$_2$     XXVII where
R$^1$ and R$^2$ together with the carbon atom to which they are attached denote a C$_4$ to C$_8$ cycloalkyl group,
R$^5$ denotes hydrogen or methyl and
Ar$^1$ is as hereinbefore defined and is free from ethylenic unsaturation.

Compounds of formula XXVI, such as 1-benzoylcyclopentanol or 1-benzoylcyclohexanol, can be prepared as described in U.S. Pat. No. 4,308,400.

Compounds of formula I where R$^1$ and R$^2$ together with the carbon atom to which they are attached, denote a cycloalkyl group and R$^3$ denotes a group of formula VIA can be prepared by reacting a compound of formula XXVI with a glycidyl ester of formula XVI.

Compounds of formula I where R$^2$ denotes a group of formula IIIA, where a denotes zero, can be prepared by reacting a compound of formula

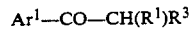 Ar$^1$—CO—CH(R$^1$)R$^3$     XXVIII with formaldehyde to give a methylol compound of formula

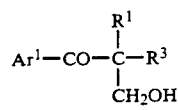

$$\text{Ar}^1-\text{CO}-\overset{\overset{\text{R}^1}{|}}{\underset{\underset{\text{CH}_2\text{OH}}{|}}{\text{C}}}-\text{R}^3 \qquad \text{XXIX}$$

and then reacting the methylol compound with an acid chloride of formula XXVII,
where
R$^1$ and R$^3$ are as hereinbefore defined, and
Ar$^1$ is as hereinbefore defined and is free from ethylenic unsaturation.

Compounds of formula XXVIII, usually benzoin ethers, are commercially available. The formation of the methylol derivative may be effected under conventional methylolating conditions and reaction of the methylol compound with the acid chloride may be carried out under conventional conditions for alcohol-acid chloride reactions.

Compounds of formula I where R$^2$ denotes a group of formula IIIA, where a denotes 1, can be prepared by reacting a methylol compound of formula XXIX with a glycidyl ester of formula XVI. Such a reaction may be carried out under conventional conditions for alcohol-epoxide reactions.

The compounds of formula I are useful for the preparation of polymeric photopolymerization initiators. Accordingly, the present invention also provides polymers of compounds of formula I as hereinbefore described. These may be homopolymers but are more usually copolymers with other monomers containing one polymerizable ethylenically unsaturated group, such as other acrylic monomers, for example esters of acrylic or methacrylic acid, styrenes and vinyl esters.

For use in electrodepositable compositions, suitable copolymers are usually copolymers of (A) a compound of formula I as hereinbefore described with (B) a monoethylenically unsaturated monomer containing an acidic or basic group and, optionally, (C) at least one other monoethylenically unsaturated monomer. Suitable acidic monomers (B) include unsaturated carboxylic acids, for example monocarboxylic acids such as acrylic acids and crotonic acid and polycarboxylic acids such as maleic acid, unsaturated sulphonic acids such as vinylsulphonic acid and unsaturated phosphonic acids such as vinylphosphonic acids. Suitable basic monomers (B) include ethylenically unsaturated materials containing a tertiary amine group, such as dialkylaminoalkyl esters of unsaturated carboxylic acids.

Preferred monomers (B) are carboxylic acids or tertiary amines containing a group of formula

 —OCOC(R$^5$)=CH$_2$     VI where R$^5$ denotes a hydrogen atom or an alkyl group of 1 to 4 carbon atoms, preferably a hydrogen atom or a methyl group.

Thus preferred monomers (B) include acrylic acid, methacrylic acid, adducts of hydroxyalkyl acrylates or methacrylates with aliphatic, cycloaliphatic or aromatic polycarboxylic acid anhydrides such as glutaric, hexahydrophthalic or phthalic anhydride, and tertiary amino-substituted alkyl esters of acrylic and methacrylic acids, particularly dialkylaminoalkyl esters of acrylic and methacrylic acids, such as dimethylaminoethyl methacrylate.

Preferred copolymers are those of (A), (B) and (C). Monomers suitable for use as (C) include acrylic monomers, styrenes, and vinyl esters. Preferred monomers (C) are styrene and esters of formula

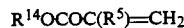 R$^{14}$OCOC(R$^5$)=CH$_2$     XXX where R$^5$ denotes a hydrogen atom or an alkyl group of 1 to 4 carbon atoms, preferably a hydrogen atom or a methyl group, and R$^{14}$ denotes an alkyl group of 1 to 10 carbon atoms, which may be substituted by a hydroxyl group. Thus preferred monomers (C) include styrene, methyl acrylate, ethyl acrylate, 2-hydroxyethyl acrylate, n-propyl acrylate, isopropyl acrylate, 2-hydroxypropyl acrylate, n-butyl acrylate, isobutyl acrylate, hexyl acrylate, ethylhexyl acrylate, the corresponding methacrylates and mixtures of two or more of the specified monomers.

Particularly preferred monomers (C) are styrene, methyl methacrylate, ethyl acrylate, 2-hydroxyethyl methacrylate, n-butyl methacrylate, isobutyl methacrylate, 2-ethylhexyl acrylate and mixtures of two or more thereof.

The copolymers of (A), (B) and (C) may be prepared from polymerizable monomer mixtures in which the amount by weight of (A) is generally from 1 to 50%, preferably 3 to 25%, especially 5 to 10%; the amount by weight of (B) is generally from 1 to 50%, preferably 3 to 25%, especially 5 to 15%; and the amount by weight of (C) is generally from 10 to 98%, preferably 50 to 95%, especially 75 to 90%.

Polymers of the invention may have number average molecular weights (Mn) from 1000 to 100,000 and weight average molecular weights (Mw) from 5000 to 250,000. Preferred polymers have Mn from 5000 to 50,000 and Mw from 10,000 to 200,000. Particularly preferred polymers have Mn from 7000 to 30,000 and Mw from 15,000 to 70,000 and from 70,000 to 180,000.

The polymers of the invention may be prepared by conventional polymerization processes using free radical polymerization initiators such as organic peroxides, hydroperoxides and azo compounds. Thus the monomer or mixture of monomers may be heated together with the initiator in solution in an organic solvent. Conventional chain transfer agents such as tert.dodecyl mercaptan can be used where desired.

The invention is illustrated by the following Examples, in which parts and percentages are by weight unless specified otherwise. Starting materials used in the Examples are prepared as follows:

1-OXO-2-METHOXY-2-(2-CARBOXYETHYL)-1,2-DIPHENYLETHANE

Benzoin methyl ether (100 g) and ethyl acrylate (50 ml) are added to dimethyl sulphoxide (150 ml) and stirred at room temperature. Aqueous sodium hydroxide solution (4 ml of 4M NaOH) is added and the reaction mixture is stirred at room temperature for 21 hours. The resulting clear solution is poured into aqueous 10% hydrochloric acid (150 ml) to produce a white precipitate, which is washed with water until the washings are neutral in pH.

The precipitate is added to a mixture of a solution of sodium hydroxide (30 g) in water (300 ml) and methanol (200 ml). The mixture is heated at 65° C. for 13 hours then poured into aqueous 10% hydrochloric acid (200 ml), when a solid is precipitated. The solid is collected, washed with water to remove traces of hydrochloric acid and redissolved in aqueous sodium hydroxide (20 g NaOH made up to 500 ml solution by addition of water). The solution obtained is washed with dichloromethane (2×200 ml) and then added dropwise to aqueous 10% hydrochloric acid (200 ml). The resulting precipitate is collected, washed with water (200 ml) until the washings are only slightly acidic in pH, and dried overnight in a vacuum oven at 40° C. to give 134 g of 1-oxo-2-methoxy-2-(2-carboxyethyl)-1,2-diphenylethane as a white powder.

ALPHA, ALPHA-DIMETHYL-ALPHA-N-MORPHOLINO-P-(2-HYDROXYETHYLTHIO)ACETOPHENONE

This compound, also known as 1-[4-(2-hydroxyethylthio)phenyl]-2-methyl-2-morpholinopropan-1-one, is prepared as described in Example B of U.S. Pat. No. 4,582,862.

1-OXO-2-ETHOXY-2-(2-ETHYLPHOSPHONOETHYL)-1,2-DIPHENYLETHANE

1-Oxo-2-ethoxy-2-(2-diethylphosphonoethyl)-1,2-diphenylethane (25 g, prepared from benzoin ethyl ether and diethyl vinyl phosphonate as described in Example 3 of U.S. Pat. No. 4,082,821) is dissolved in ethanol (200 ml). Sodium hydroxide (20 g) is added to the solution and the mixture is heated under reflux for 3 hours. The ethanol is removed by rotary evaporation, water is added, and the mixture is washed with diethyl ether (4×100 ml) to remove unreacted starting material. Concentrated hydrochloric acid is added to the aqueous mixture until the pH is zero. The resulting mixture is washed with ether, water is evaporated and the residue is recrystallised from a mixture of acetone and ether to give 12.5 g of product, a compound of formula XVIII where $R^1$ is ethoxy, $R^3$ and $Ar^1$ are each phenyl, $R^7$ is —$CH_2CH_2$— and $R^8$ is —$CH_2CH_3$.

1-OXO-2-METHOXY-2-(2-ETHYLPHOSPHONOETHYL)-1,2-DIPHENYLETHANE

1-Oxo-2-methoxy-2-(2-diethylphosphonoethyl)-1,2-diphenylethane (100 g, prepared from benzoin methyl ether and diethyl vinyl phosphonate as described in Example 1 of U.S. Pat. No. 4,082,821) is dissolved in methanol (400 ml). Sodium hydroxide (40 g) is added to the solution and the mixture is heated under reflux for 2 hours. The methanol is removed by rotary evaporation, water (300 ml) is added and the mixture is washed with diethyl ether (4×100 ml). The resulting aqueous mixture is cooled to 0° C., and concentrated hydrochloric acid is added until the pH is zero, when a solid is precipitated. This is washed with water and then stirred together with acetone (300 ml), when sodium chloride remains as undissolved solid. The sodium chloride is filtered off and acetone is removed by evaporation to give a solid which is recrystallised from a mixture of acetone and ether to give 90 g of product, a compound of formula XVIII where $R^1$ is methoxy, $R^3$ and $Ar^1$ are each phenyl, $R^7$ is —$CH_2CH_2$— and $R^8$ is —$CH_2CH_3$.

EXAMPLE 1

Preparation of Acrylic Monomer I

1-Oxo-2-methoxy-2-(2-carboxyethyl)-1,2-diphenylethane (10.0 g), 2,6-di-tert.butyl-p-cresol (0.2 g) and chromium III trisoctanoate (5% solution in ligroin; 0.2 g) are dissolved in toluene (150 g) and the mixture is heated to 110° C. Glycidyl acrylate (8.58 g) is added dropwise to the solution over 30 minutes. Heating at 110° C. is continued for 6 hours until the epoxy value of the mixture falls below 0.2 equiv/kg. The toluene is removed under reduced pressure to give 26.1 g of an oil—a compound of formula I where $R^1 = OCH_3$, $R^2 =$ a group of formula XI where $R^5 = H$, and $R^3$ and $Ar^1 = $phenyl; $^1$HNMR (acetone-$d_6$), $\delta$1.8–2.8 (m-4H), 3.25(s-3H), 4.1–4.5(m-5H), 5.90–6.30 (m-3H), 7.90–8.00(m-10H); IR (liquid film) 3480, 3060, 2950, 2830, 1725, 1675, 1595, 1575, 1495, 1445, 1405, 1240, 1180, 1105, 1075, 985, 850, 810, 760, 745, 705, 645 cm$^{-1}$.

EXAMPLE 2

Preparation of Acrylic Monomer II

Alpha, alpha-dimethyl-alpha-N-morpholino-p-(2-hydroxyethylthio)acetophenone (10.0 g) and dibutyltindilaurate (0.05 g) are dissolved in dry toluene (75 ml) in a vessel previously purged with nitrogen. The mixture is heated to 70° C. and 2-isocyanatoethyl methacrylate (4.5 g) in dry toluene (25 ml) with 2,6-di-t-butyl-p-cresol (0.1 g) are added dropwise over 1 hour. The reaction mixture is then heated at 70° C. for a further 2 hours. Absence of an isocyanate band in the infra-red spectrum indicates that the reaction has gone to completion. The toluene is removed under reduced pressure at 80° C. to give 15.6 g of an oil—a compound of formula I where $R^1$ and $R^2 = CH_3$, $R^3 = $N-morpholino and $Ar^1 = $phenyl p-substituted by a group of formula XIII where $R^5 = CH_3$, $^1$HNMR (acetone-$d_6$) 1.35(s-6H), 1.95(m-3H), 2.55(m-2H), 3.5(m-6H), 4.2(m-8H), 5.5–6.1 (m-2H), 7.95(q-4H) $\delta$; IR (liquid film) 3350, 2950, 2850, 1715, 1667, 1582, 1525, 1450, 1383, 1360, 1320, 1295, 1258, 1160, 1120, 1090, 975, 880, 855, 825, 815, 778, 755, 735, 695 cm$^{-1}$.

EXAMPLE 3

Preparation of Acrylic Monomer III

A reaction vessel is purged with nitrogen and then charged with 1-oxo-2-methoxy-2-(2-carboxyethyl)-1,2-diphenylethane (10.0 g), N,N-dimethyl-4-aminopyridine (0.74 g) and dichloromethane (100 ml). 2-Isocyanatoethyl methacrylate (5.2 g) and dichloromethane (50 ml) are added and the mixture is stirred at room temperature for 4½ hours under a very slow nitrogen purge. At the end of this time the isocyanate band in the infra-red spectrum of the solution has disappeared. The solution is washed with aqueous 10% hydrochloric acid (100 ml) and saturated aqueous sodium bicarbonate solution (100 ml) and dried over magnesium sulphate. The dichloromethane is removed under reduced pressure to give 12.95 g of a yellow oil—a compound of formula I where $R^1=OCH_3$, $R^2=$a group of formula X where $R^5=CH_3$, and $R^3$ and $Ar^1=$phenyl. NMR ($CDCl_3$) 1.95 (m-3H), 2.2–2.9 (m-4H), 3.25(s-3H), 3.5(t-2H), 4.2(t-2H), 5.60–6.15(m-2H), 7.35–7.95 (m-10H) δ; IR (liquid film) 3340, 3080, 2950, 2830, 1715, 1675, 1635, 1595, 1550, 1445, 1320, 1295, 1240, 1165, 1105, 1080, 1045, 850, 815, 760, 740, 700, 645 cm$^{-1}$.

EXAMPLE 4

Preparation of Acrylic Monomer IV

1-Oxo-2-ethoxy-2-(2-ethylphosphonoethyl)-1,2-diphenylethane (10.0 g) is dissolved in toluene (100.0 g) and the solution is heated to 110° C. Glycidyl acrylate (3.2 g), chromium III trisoctanoate (5% solution in ligroin; 0.1 g) and 2,6-di-tert.-butyl-p-cresol (0.1 g) are added. After heating for 2 hours at 110° C., the epoxy value falls to zero. The toluene is removed under reduced pressure to give 12.4 g of an oil—a compound of formula I where $R^1=OCH_2CH_3$, $R^2=$a group of formula XII where $R^5=H$, and $R^3$ and $Ar^1=$phenyl; NMR (acetone-d$_6$) 1.0–1.4 (m-6H) 2.2–2.8 (m-4H), 3.5–4.4(m-9H), 5.95–6.35(m-3H), 7.45–8.05(m-10H) δ; IR (liquid film) 3460, 3060, 2980, 2880, 1727, 1685, 1597, 1495, 1450, 1410, 1250, 1185, 1100, 1075, 1035, 860, 812, 765, 705, 655 cm$^{-1}$.

EXAMPLE 5

Preparation of Acrylic Monomer V

1-Oxo-2-methoxy-2-(2-ethylphosphonoethyl)-1,2-diphenylethane (10.0 g) is dissolved in toluene (200 ml) and the solution is heated to 110° C. Glycidyl acrylate (3.0 g), chromium III trisoctanoate (5% solution in ligroin; 0.2 g) and 2,6-di-t-butyl-p-cresol (0.2 g) are added. After heating for 5 hours at 110° C., the epoxy value of the solution has dropped to zero. The toluene is removed under reduced pressure to give 9.8 g of an oil—a compound of formula I where $R^1=OCH_3$, $R^2=$a group of formula XII where $R^5=H$, and $R^3$ and $Ar^1=$phenyl; $^1$HNMR(acetone-d$_6$) 1.0–1.4(m-3H), 2.0–2.9 (m-4H), 3.30(s-3H), 3.15–4.15(m-7H), 5.95–6.33(m-3H), 7.45(m-5H), 8.05(m-5H) δ; IR (liquid film) 3460, 3065, 2960, 2840, 1730, 1680, 1600, 1580, 1495, 1450, 1410, 1220, 1050, 892, 862, 815, 765, 710, 650 cm$^{-1}$.

EXAMPLE 6

2-n-Butoxyethanol (67 g) is heated to 80° C. under a nitrogen atmosphere. A mixture of methyl methacrylate (60.0 g), n-butyl methacrylate (25.5 g), 2-(dimethylamino)ethyl methacrylate (DMAEMA) (8.0 g), Acrylic Monomer I (6.5 g) and azobis(isobutyronitrile) (AIBN) (1.35 g) is added dropwise to the solvent over four hours. When monomer addition is complete, the reaction mixture is heated at 80° C. for a further 20 minutes before adding a further quantity of AIBN (0.15 g). After heating at 80° C. for a further 30 minutes, the polymer solution is allowed to cool to room temperature. The copolymer solution has a non-volatile content of 60% by weight, indicating essentially complete conversion of the monomers to polymer, and an amine value of 0.37 eq/kg. The copolymer has a number average molecular weight of 13636 and a weight average molecular weight of 28859.

EXAMPLE 7

The procedure of Example 6 is repeated, replacing the ingredients by

| | |
|---|---|
| 2-n-butoxyethanol | 100 g |
| methyl methacrylate | 92 g |
| n-butyl methacrylate | 40 g |
| DMAEMA | 12 g |
| Acrylic Monomer II | 10 g |
| AIBN (0.77 g initially, 0.1 g on further addition) | 0.87 g |

The resulting co-polymer has an amine value of 0.48 equiv/kg, a number average molecular weight of 29,828 and a weight average molecular weight of 67,946.

EXAMPLE 8

The procedure of Example 6 is repeated, replacing the ingredients by

| | |
|---|---|
| 2-n-butoxyethanol | 67.0 g |
| methyl methacrylate | 60.0 g |
| n-butyl methacrylate | 25.5 q |
| DMAEMA | 8.0 g |
| Acrylic Monomer I | 6.5 g |
| AIBN (1.35 g initially, further 0.15 g) | 1.5 g |

The polymer obtained has an amine value of 0.33 eq/kg and a non-volatile content of 57.2%. It has a number average molecular weight of 12,340 and a weight average molecular weight of 29,693.

EXAMPLE 9

2-n-butoxyethanol (100.0 g) is heated to 80° C. under a nitrogen atmosphere. A mixture of methyl methacrylate (50.0 g), isobutyl methacrylate (25.5 g), DMAEMA (8.0 g), acrylic acid (10.0 g), Acrylic Monomer I (6.5 g) and AIBN (1.6 g) is added dropwise to the solvent over 4 hours. When monomers addition is complete, the reaction mixture is heated for a further 20 minutes at 80° C., AIBN (0.15 g) is added and then heating is continued at 80° C. for a further 30 minutes. The copolymer solution obtained has a non-volatile content of 49% by weight, indicating essentially complete conversion of monomers to polymer. The copolymer has an amine value of 0.33 eq/kg, an acid value of 0.66 eq/kg, a number average molecular weight of 9060 and a weight average molecular weight of 23541.

EXAMPLE 10

The procedure of Example 6 is repeated, replacing the ingredients by

| | |
|---|---|
| 2-n-butoxyethanol | 67.0 g |
| methyl methacrylate | 60.0 g |
| n-butyl methacrylate | 25.5 g |
| DMAEMA | 8.0 g |
| Acrylic Monomer I | 6.5 g |
| AIBN (1.6 g + further 0.15 g) | 1.75 g |

The resulting copolymer solution has a solids content of 58.9% and an amine value of 0.43 equiv./kg. The copolymer has a number average molecular weight of 13,047 and a weight average molecular weight of 25,577.

EXAMPLE 11

A mixture of methyl methacrylate (60 g), n-butyl methacrylate (25.5 g), DMAEMA (8.0 g), Acrylic Monomer III (6.5 g), AIBN (2.0 g), one drop of tert-.dodecylmercaptan as chain transfer agent and 2-n-butoxyethanol (67 g) is heated to 80° C. under nitrogen and maintained at 80° C. for 20 minutes. Further 2-n-butoxyethanol (33 g) is added and the heating at 80° C. is continued for 4½ hours. More AIBN (0.1 g) is added and heating at 80° C. is continued for a further hour. The copolymer solution obtained has a solids content of 48.7% and an amine value of 0.31 equiv/kg. The copolymer has a number average molecular weight of 9093 and a weight average molecular weight of 39,617.

EXAMPLE 12

The procedure of Example 6 is repeated, replacing the ingredients by

| | |
|---|---|
| 2-n-butoxyethanol | 67.0 g |
| methyl methacrylate | 62.0 g |
| n-butyl methacrylate | 27.5 g |
| DMAEMA | 4.0 g |
| Acrylic Monomer I | 6.5 g |
| AIBN (1.6 g + further 0.15 g) | 1.75 g |
| tert.dodecylmercaptan (chain transfer agent) | 0.05 g |

The resulting copolymer solution has an amine value of 0.20 eq/kg and a solids content of 60%.

The copolymer has a number average molecular weight of 15,612 and a weight average molecular weight of 39,933.

EXAMPLE 13

The procedure of Example 6 is repeated, replacing the ingredients by

| | |
|---|---|
| 2-n-butoxyethanol | 100 g |
| methyl methacrylate | 100 g |
| n-butyl methacrylate | 28 g |
| DMAEMA | 12 g |
| Acrylic Monomer IV | 10 g |
| AIBN | 0.87 g |

The copolymer solution obtained has a solids content of 50.3% and an amine value of 0.47 equiv./kg. The copolymer has a number average molecular weight of 15,762 and a weight average molecular weight of 47,739.

EXAMPLE 14

2-n-butoxyethanol (67.0 g) is heated to 80° C. under nitrogen. A mixture of methyl methacrylate (60.0 g), n-butyl methacrylate (25.5 g), DMAEMA (8.0 g), Acrylic Monomer I (6.5 g) and AIBN (1.6 g) is added over 4 hours. The heating is continued at 80° C. for a further 20 minutes, a further quantity of AIBN (0.2 g) is added and heating at 80° C. is continued for a further 30 minutes. More AIBN (0.2 g) is added and the mixture is heated at 80° C. for 30 minutes. The resulting copolymer solution has a solids content of 55.6% and an amine value of 0.35 equiv./kg. The copolymer has a number average molecular weight of 11,873 and a weight average molecular weight of 28,495.

EXAMPLE 15

The procedure of Example 6 is repeated, replacing the ingredients by

| | |
|---|---|
| 2-n-butoxyethanol | 100 g |
| methyl methacrylate | 100 g |
| n-butyl methacrylate | 40 g |
| DMAEMA | 12 g |
| tert.butyl perbenzoate (1.40 g + further 0.15 g) | 1.55 g |
| Acrylic Monomer V | 5.1 g |

The copolymer solution obtained has a solids content of 51.3% and an amine value of 0.52 equiv./kg.

EXAMPLE 16

The procedure of Example 6 is repeated, replacing the ingredients by

| | |
|---|---|
| 2-n-butoxyethanol | 67.0 g |
| methyl methacrylate | 60.0 g |
| n-butyl methacrylate | 25.5 g |
| DMAEMA | 8.0 g |
| Acrylic Monomer I | 6.5 g |
| AIBN (0.9 g + 0.1 g) | 1.0 g |

The resulting copolymer solution has an amine value of 0.35 equiv./kg and a solids content of 54%. The copolymer has a number average molecular weight of 14,341 and a weight average molecular weight of 37,608.

EXAMPLE 17

A mixture of 2-n-butoxyethanol (66.0 g) and tert-.dodecylmercaptan (0.05 g) is heated to 80° C. under nitrogen. A mixture of methyl methacrylate (61.3 g), n-butyl methacrylate (24.2 g) DMAEMA (8.0 g), Acrylic Monomer I (6.5 g) and AIBN (1.8 g) is added dropwise over 4 hours. The resulting mixture is heated at 80° C. for 20 minutes, further AIBN (0.2 g) is added and the heating at 80° C. continued for a further 30 minutes. The copolymer solution obtained has a solids content of 61% and an amine value of 0.34 equiv./kg. The copolymer has a number average molecular weight of 7201 and a weight average molecular weight of 15,849.

EXAMPLE 18

The procedure of Example 6 is repeated, replacing the ingredients by

| | |
|---|---|
| 2-n-butoxyethanol | 67.0 g |
| methyl methacrylate | 60.0 g |
| ethyl acrylate | 25.5 g |
| DMAEMA | 8.0 g |
| Acrylic Monomer I | 6.5 g |
| 2.0 g AIBN (1.8 g + further 0.2 g) | 2.0 g |

The copolymer solution obtained has an amine value of 0.37 equiv./kg and a solids content of 58%. The copolymer has a number average molecular weight of 18,481 and a weight average molecular weight of 37,764.

EXAMPLE 19

Preparation of Acrylic Monomer VI

1-Benzoylcyclohexanol (10.21 g, 0.05 mol) is dissolved in dichloromethane (50 ml). Triethylamine (8.36 ml, 0.06 mol) is added and the mixture is stirred for 15 minutes, then cooled by an ice bath. Acryloyl chloride (4.87 ml, 0.06 mol) is added dropwise to the cooled mixture. The resulting mixture is stirred for 15 minutes while cooling in the ice bath, stirred for 30 minutes at room temperature and then poured into water. The organic phase is washed with aqueous sodium bicarbonate, water and brine and dried over magnesium sulphate. Evaporation of solvent from the dried mixture leaves a viscous oil which solidifies on standing to give a white solid. This is washed with petrol and dried to give a 55% yield of a compound of formula I where $R^1$ and $R^2$ together with the attached carbon denote cyclohexyl, $R^3$ denotes a group of formula VI and $Ar^1$ denotes phenyl.

IR (KBr disc): 2920, 1720, 1675, 1625, 1580, 1450, 1400, 980, 960 $cm^{-1}$.

$^1H$ NMR (60 MHZ) δ(ppm): 8.0–7.8 (m-2H), 7.5–7.2 (m-3H), 6.3–5.7 (m-3H), 2.5–1.5 (m-10H).

EXAMPLE 20

A monomer mixture of 2-hydroxyethyl methacrylate (20 parts), DMAEMA (5 parts), methacrylic acid (5 parts), methyl methacrylate (65 parts) and Acrylic Monomer VI (5 parts) is dissolved together with AIBN (0.3 part) in ethyl acetate (300 parts). The solution obtained is heated at 65° C. for 20 hours, then diluted with chloroform (50 ml) and poured into hexane (3 litres). The precipitate obtained is filtered off and dried under vacuum to give a copolymer having a number average molecular weight of 22,759, a weight average molecular weight of 173,672 and an amine value of 0.27 equiv./kg.

EXAMPLE 21

The procedure of Example 20 is repeated using a monomer mixture of 2-hydroxyethyl methacrylate (20 parts), DMAEMA (10 parts), methacrylic acid (5 parts), 2-ethylhexyl acrylate (20 parts), styrene (35 parts) and Acrylic Monomer VI (10 parts) dissolved together with AIBN (0.5 part) in ethyl acetate (150 parts). The resulting copolymer has a number average molecular weight of 23,941, a weight average molecular weight of 74,518 and an amine value of 0.74 equiv./kg.

EXAMPLE 22

Preparation of Acrylic Monomer VII

Paraformaldehyde (1.8 g, 1.2 equivs. HCHO) is added to a stirred solution of benzoin methyl ether (11.3 g, 0.05 mol) in dimethyl sulphoxide (100 ml) with potassium hydroxide (0.15 g) in ethanol (2 ml). The mixture is heated under nitrogen at 40° C. for 3 hours. After cooling to room temperature and neutralizing, the mixture is extracted into ethyl acetate (3×50 ml), washed with brine, dried over magnesium sulphate and evaporated to give a viscous oil which solidifies on cooling to yield white crystals of the methylol derivative of benzoin methyl ether (95% yield); IR (KBr disc): 3300, 1680, 1260, 1060 $cm^{-1}$ $^1H$ NMR (60 MHZ) δ(ppm): 8.1–7.9 (m, 2H), 7.6–7.2 (m, 8H), 4.6–4.0 (m, 2H), 3.5 (s, 3H), 2.1 (1H).

The methylol derivative (10.25, 0.04 mol) is dissolved in dichloromethane (80 ml) and triethylamine (6.69 ml, 0.048 mol) is added. The mixture is stirred for 15 minutes at room temperature, cooled to 0° C., and acryloyl chloride (3.9 ml, 0.048 mol) is added. The reaction mixture is stirred at 0° C. for 30 minutes, then at room temperature for 1 hour. The reaction is terminated by pouring into water, the organic phase is washed in aqueous sodium bicarbonate, then brine, dried over magnesium sulphate and the solvent is evaporated. The resulting yellow oil crystallises on standing and is recrystalised from ethanol to yield white crystals—a 60% yield of a compound of formula I where $R^1=OCH_3$, $R^2=CH_2OCOCH=CH_2$, and $R^3$ and $Ar^1$ each denote phenyl. IR (KBr disc): 1720, 1660, 1620, 1440, 1400, 980, 920 $cm^{-1}$. $^1H$ NMR (60 MHZ) δ(ppm): 8.1–7.85 (m-2H), 7.6–7.2 (m-8H), 6.3–5.7 (m-3H), 5.3–4.6 (two d-2H), 3.4(s-3H).

EXAMPLE 23

The procedure of Example 20 is repeated using a monomer mixture of 2-hydroxyethyl methacrylate (20 parts), DMAEMA (5 parts), methacrylic acid (5 parts), 2-ethylhexyl acrylate (10 parts), styrene (55 parts) and Acrylic Monomer VII (5 parts) dissolved together with AIBN (0.3 part) in 2-n-butoxyethanol (150 parts). The resulting copolymer has a number average molecular weight of 18,132, a weight average molecular weight of 59,800 and an amine value of 0.36 equiv./kg.

EXAMPLE 24

The procedure of Example 20 is repeated using a monomer mixture of 2-hydroxyethyl methacrylate (20 parts), DMAEMA (10 parts), methacrylic acid (5 parts), 2-ethylhexyl acrylate (20 parts), styrene (40 parts) and Acrylic Monomer VII (5 parts) dissolved together with 2,2'-azobis(2-methylbutyronitrile) (0.5 part) in ethyl acetate (150 parts). The resulting copolymer has a number average molecular weight of 33,103, a weight average molecular weight of 133,949 and an amine value of 0.80 equiv./kg.

EXAMPLE 25

The procedure of Example 20 is repeated using a monomer mixture of 2-hydroxyethyl methacrylate (20 parts), DMAEMA (10 parts), methacrylic acid (5 parts), 2-ethylhexyl acrylate (20 parts), styrene (35 parts) and Acrylic Monomer VII (10 parts) dissolved together with AIBN (0.5 part) in ethy acetate (150 parts). The resulting copolymer has a number average molecular weight of 25,374, a weight average molecular weight of 124,338 and an amine value of 0.85 equiv./kg.

EXAMPLE 26

A mixture of 2,2-bis(4-(3-acryloyloxy-2-hydroxypropoxy)-phenyl)propane (49 parts) and Acrylic Monomer VII (1 part) is coated onto tinplate as a film having a thickness of 24 micrometres. Irradiation of the film using a 5000 w metal halide lamp at a distance of 75 cm gives a tack-free coating after 10 seconds.

EXAMPLE 27

Example 26 is repeated using Acrylic Monomer VI (1 part) in place of Acrylic Monomer VII. A tack-free coating is obtained after irradiation for 20 seconds.

EXAMPLE 28

Example 26 is repeated using pentaerythritol triacrylate (49 parts) in place of the bisacryloyloxy compound used in that Example. A tack-free coating is obtained after irradiation for 60 seconds.

What is claimed is:

1. A copolymer of at least two monoethylenically unsaturated monomers, at least one of said monomers being a monoethylenically unsaturated compound of formula I $$Ar^1-CO-\underset{\underset{R^2}{|}}{\overset{\overset{R^1}{|}}{C}}-R^3 \qquad I$$

where $R^1$ denotes an alkyl or alkoxy group of 1 to 10 carbon atoms, $R^2$ denotes a group of formula II, III or IIIA:

$$-X-O-R^4-OCOC(R^5)=CH_2 \qquad II$$

$$-X-N-R^6-OCOC(R^5)=CH_2 \qquad III$$

$$-CH_2(OCH_2CH(OH)CH_2)_aOCOC(R^5)=CH_2 \qquad IIIA$$

$R^3$ denotes a monovalent aromatic group of 6 to 20 carbon atoms, linked through an aromatic carbon atom to the indicated carbon atom, a hydroxyl group, a tertiary amine group linked through the amino nitrogen to the indicated carbon atom, or a group of formula VI or VIA:

$$-OCOC(R^5)=CH_2 \qquad VI$$

$$-OCH_2CH(OH)CH_2OCOC(R^5)=CH_2 \qquad VIA$$

$R^4$ denotes an alkylene group of 1 to 4 carbon atoms, which is unsubstituted or substituted by a hydroxyl group or by an acyloxy group of 2 to 20 carbon atoms, $R^5$ denotes a hydrogen atom or an alkyl group of 1 to 4 carbon atoms, $R^6$ denotes an alkylene group of 1 to 4 carbon atoms, X denotes a group of formula IV or V $$-R^7-CO- \qquad IV$$

$$-R^7-\underset{\underset{OR^8}{|}}{\overset{\overset{O}{\|}}{P}}-(O-CO)_a \qquad V$$

$R^7$ denotes an alkylene group of 1 to 4 carbon atoms, $R^8$ denotes an alkyl group of 1 to 4 carbon atoms, a denotes zero or 1, and $Ar^1$ denotes a monovalent aromatic group of 6 to 20 carbon atoms linked through an aromatic carbon atom to the indicated carbonyl group, with the provisos that (i) $R^2$, $R^3$ or $Ar^1$ contains a group of the formula $$-OCOC(R^5)=CH_2 \qquad VI$$

(ii) when $R^2$ denotes a group of formula II, a denotes zero, (iii) when $R^2$ denotes a group of formula III, a denotes 1, and (iv) when $R^2$ denotes a group of formula IIIA, $R^3$ denotes said monovalent aromatic group of 6 to 20 carbon atoms.

2. A copolymer of at least two monoethylenically unsaturated monomers, at least one of said monomers being (A) a compound according to claim 1 and at least one of said monomers being (B) a monomer containing an acidic or basic group.

3. A copolymer of at least two monoethylenically unsaturated monomers, at least one of said monomers being (A) a compound of the formula I according to claim 1 wherein $R^1$ is an alkyl or alkoxy group of 1 to 4 carbon atoms and at least one of said monomers being (B) a monomer containing an acidic or basic group.

4. A copolymer of at least two monoethylenically unsaturated monomers, at least one of said monomers being (A) a compound according to claim 1 of the formula I wherein $R^2$ is a group of the formula II or III wherein $R^4$ is a group of the formula VII $$-CH_2CH(OH)CH_2- \qquad VII$$

$R^6$ is an ethylene or propylene group and X is a group of the formula IV or V wherein $R^7$ is an ethylene or propylene group and $R^8$ is a methyl or ethyl group and at least one of said monomers being (B) a monomer containing an acidic or basic group.

5. A copolymer of at least two monoethylenically unsaturated monomers, at least one of said monomers (A) being a compound according to claim 1 of the formula I wherein $R^3$ is a phenyl group or a monovalent nitrogen heterocyclic group of 4 or 5 carbon atoms linked through a ring tertiary nitrogen atom to the indicated carbon atom and at least one of said monomers being (B) a monomer containing an acidic or basic group.

6. A copolymer of at least two monoethylenically unsaturated monomers, at least one of said monomers (A) being a compound according to claim 1 of the formula I wherein $Ar^1$ is a phenyl group which is unsubstituted or substituted by an alkyl, alkoxy or alkylthio group of 1 to 4 carbon atoms, or a group of the formula VIII or IX $$-Y-R^{10}-(OR^{11})_mOCOC(R^5)=CH_2 \qquad VIII$$

$$-Y-R^{10}OCONHR^6OCOC(R^5)=CH_2 \qquad IX$$

wherein $R^{10}$ is an alkylene group of 1 to 4 carbon atoms, $R^{11}$ is an alkylene group of 1 to 4 carbon atoms which is unsubstituted or substituted by a hydroxyl group or by an acyloxy group of 2 to 20 carbon atoms, Y is an oxygen or sulfur atom, and m is 0 or 1, and at least one of said monomers being (B) a monomer containing an acidic or basic group.

7. A copolymer according to claim 2, in which (B) is a carboxylic acid or tertiary amine containing a group of formula $$-OCOC(R^5)=CH_2 \qquad VI$$

where $R^5$ denotes a hydrogen atom or an alkyl group of 1 to 4 carbon atoms.

8. A copolymer of at least three monoethylenically unsaturated monomers, at least one of said monomers being (A) a compound according to claim 1, at least one of said monomers being (B) a monomer containing an acidic or basic group and at least one of said monomers being (C) styrene or an ester of formula $$R^{14}OCOC(R^5)=CH_2 \quad \text{XXXI}$$

where $R^5$ denotes a hydrogen atom or an alkyl group of 1 to 4 carbon atoms and $R^{14}$ denotes an alkyl group of 1 to 10 carbon atoms or an alkyl group of 1 to 10 carbon atoms substituted by a hydroxyl group.

9. A copolymer of at least two monoethylenically unsaturated monomers, at least one of said monomers being (A) a compound according to claim 1 of the formula I wherein $R^1$ denotes a methoxy group, $R^2$ denotes a group of formula X or XI $$-CH_2CH_2CONHCH_2CH_2OCOC(R^5)=CH_2 \quad \text{X}$$

$$-CH_2CH_2COOCH_2CH(OH)CH_2OCOC(R^5)=CH_2 \quad \text{XI}$$

$R^5$ denotes a hydrogen atom or a methyl group, and $R^3$ and $Ar^1$ each denotes an unsubstituted phenyl group; or $R^1$ denotes a methoxy or ethoxy group, $R^2$ denotes a group of formula $$-CH_2CH_2-\overset{\overset{O}{\|}}{\underset{OCH_2CH_3}{P}}-OCH_2CH(OH)CH_2OCOC(R^5)=CH_2 \quad \text{XII}$$

$R^5$ denotes a hydrogen atom or a methyl group, and $R^3$ and $Ar^1$ each denote an unsubstituted phenyl group; or $R^1$ denotes a methoxy group, $R^2$ denotes a group of formula $$-CH_2OCOC(R^5)=CH_2 \quad \text{XIVA}$$

$R^5$ denotes a hydrogen atom or a methyl group, and $R^3$ and $Ar^1$ each denote an unsubstituted phenyl group, and at least one of said monomers being (B) a monomer containing an acidic or basic group.

* * * * *